US00PP19152P3

(12) United States Plant Patent
Gabay

(10) Patent No.: US PP19,152 P3
(45) Date of Patent: Aug. 26, 2008

(54) MANGO TREE NAMED 'LEOPOLD'

(50) Latin Name: *Mangifera indica L.*
Varietal Denomination: Leopold

(76) Inventor: William John Gabay, 1605 NE. 171 St., North Miami Beach, FL (US) 33162

( * ) Notice: Subject to any disclaimer, the term of this patent is extended or adjusted under 35 U.S.C. 154(b) by 176 days.

(21) Appl. No.: 11/199,894

(22) Filed: Aug. 9, 2005

(65) Prior Publication Data

US 2007/0039080 P1 Feb. 15, 2007

(51) Int. Cl.
*A01H 5/00* (2006.01)

(52) U.S. Cl. ..... Plt./159
(58) Field of Classification Search ..... Plt./159
See application file for complete search history.

(56) References Cited

U.S. PATENT DOCUMENTS

| | | | |
|---|---|---|---|
| PP119 | P | 1/1935 | Wilkinson |
| PP451 | P | 2/1941 | Fascell |
| PP3,181 | P | 5/1972 | Sturrock |
| PP7,140 | P | 2/1990 | Brooks |
| PP7,141 | P | 2/1990 | Mitchell |
| PP7,158 | P | 2/1990 | Mitchell |
| PP2,391 | P | 4/1994 | Sturrock |
| PP9,005 | P | 12/1994 | Chang |

OTHER PUBLICATIONS

Morton, J., Fruits of warm climates, Mango, 1987, Miami, Florida, http://www.hort.purdue.edu/newcrop/mprton/mango_ars.html.
Mango Botany and Toxonomy, http://www.horticulture-world.net/botany–toxony.htm.

*Primary Examiner*—Kent L. Bell
(74) *Attorney, Agent, or Firm*—Maritn Fleit; Paul D. Bianco; Fleit GIbbons Gutman Bongini & Bianco , PL

(57) ABSTRACT

The present invention provides a new and distinct variety of mango. The new mango tree, named 'Leopold', produces fruit distinguishable from other mango varieties by its quality of flesh which includes only a small amount of fiber attached to the husk of the freestone seed. The average weight of the mango fruit is about 13–18 ounces when ripe and has a smooth skin which is brightly colored. The new mango fruit has good storage and handling qualities.

5 Drawing Sheets

Genus species: *Mangifera indica. L.*
Denomination: 'Leopold'.

BACKGROUND OF THE INVENTION

A mango tree is a medium to large (about 30 to 90 feet) evergreen with a symmetrical, rounded canopy ranging from low and dense to upright and open. The bark of the mango tree is usually dark grey-brown to black, generally smooth, and superficially cracked or fissured. The mango tree forms a long unbranched long taproot plus a dense mass of superficial feeder roots. In deep soil, the taproot descends to a depth of about 20 feet. The profuse, wide-spreading feeder roots also send many anchor roots which penetrate for several feet.

The leaves of a typical mango tree may be about 4 to 12 inches in length and ¾ to 2 inches in width. The leaves may have a variety of shapes such as oval-lanceolate, lanceolate, oblong, linear-oblong, ovate, obovate-lanceolate, or roundish-oblong. Hermaphrodite and male flowers are produced in the same panicle. The flowers are usually yellowish or reddish in color and are borne in profuse, showy, erect, pyramidal, branched clusters in the fruits. The size of both the male and hermaphrodite flowers varies from about ¼ to ½ inches in diameter.

The mango fruit is generally a compressed, fleshy drupe. It varies considerably in size, shape, color, fiber content, flavor, and taste. The fruit may be nearly round, oval, ovoid-oblong, or somewhat kidney-shaped, and is usually more or less lop-sided. The fruit ranges from 2½ to 10 inches in length and from a few ounces to 4 or 5 pounds. The skin of the fruit is leathery, waxy, smooth, fairly thick, aromatic and ranges from light- or dark-green to clear yellow, yellow-orange, yellow and reddish-pink, or generally blushed with bright- or dark-red or purple-red, with fine yellow, greenish or reddish dots, and thin or thick whitish, gray, or purplish bloom, when fully ripe. The most characteristic feature of the fruit is the formation of a small conical projection developing laterally at the proximal end of the fruit, known as the beak. The beak may be prominent in some, less in others, and in some varieties it is represented merely as a dot.

SUMMARY OF THE INVENTION

The present invention relates to a new variety of tropical mango which was discovered growing in a cultivated area in North Miami Beach, Fla. This new variety of tropical mango presumably originated as a naturally occurring chance seedling growing on its own roots. Since the parent tree is old, and no budunion is evident thereon, the origin of the parent tree is not known with any certainty. At the time of discovery, the tree was in a state of severe physical decline, and was resuscitated by the inventor. The fruit of the discovered mango tree is characterized as having a similar aroma, flavor, taste, texture of flesh, and lack of fiber as the variety of mango named, 'Bombay Green'. Relative to the 'Bombay Green', the mango of the present invention has better keeping qualities. In other words, the mango of the present invention has an extended shelf life, a brightly colored fruit, a resistance to bruising, a resistance to wind, and a degree of resistance to anthracnose. The new mango tree produces fruit that matures in July and August in North Miami Beach, Fla. The fruit as described usually falls to the ground at full maturity and ripens in 5–10 days at 75° F. to 80° F. The fruit can be held under controlled storage conditions for about 15–30 days. The new tropical mango tree was asexually reproduced by the inventor by grafting a scion of the tree to seedlings of the variety 'Turpentine'. In particular, the inventor acquired seedling plants of the variety 'Turpentine' and at the family residence in North Miami Beach, Fla., grafted scions of the new mango variety 'Leopold' onto the stock 'Turpentine' seedlings, using the veneer grafting method, asexually reproducing the new variety. Subsequent grafting by the inventor, using the modified cleft tip grafting method, produced progeny of the parent and first generation grafts, which confirmed that all progeny in all respects observable were identical to the parent tree.

BRIEF DESCRIPTION OF THE DRAWINGS

The accompanying photographs show the tree and fruit of the present invention. In such photographs.

DETAILED BOTANICAL DESCRIPTION

The present invention relates to a new variety of tropical mango which was discovered growing in a cultivated area in North Miami Beach, Fla. The age of the parent tree is unknown, but it is believed to be at least 45 years old. The new mango tree is named 'Leopold'.

Figure 1:
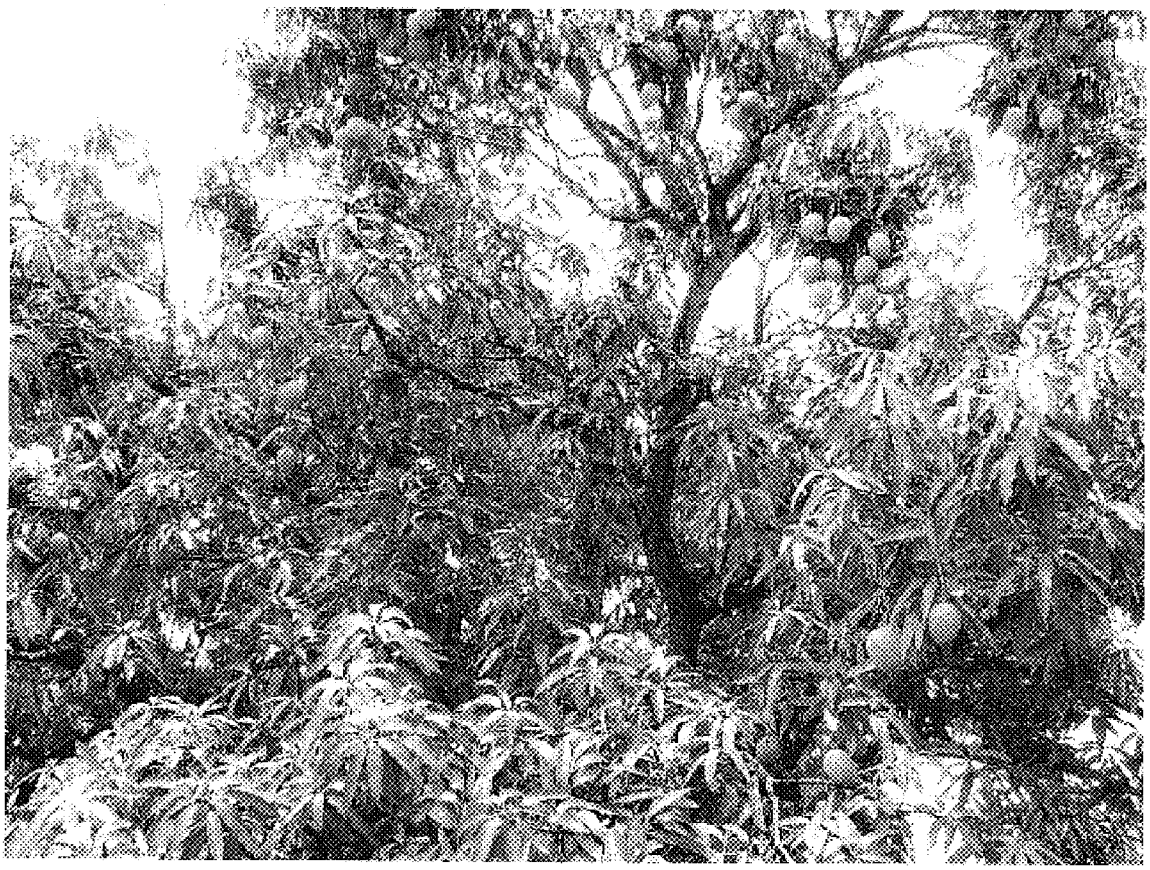
FIG. 1 shows a new tropical mango tree of the present invention.

Referring now to the drawing figures, there is shown in FIG. 1 the mango tree of the present invention. The mature tree has a crown described as broadly pyramidal with a crown diameter of approximately 25 feet, north to south, and a trunk circumference of approximately three feet, and a total height of almost 30 feet. The instant tree's bark on the main trunk and limbs is very rough and has large cracks in the bark, with a color reference of Grayed Yellow 161D (all color codes herein follow The Royal Horticultural Society's color numbering system). In 2005, the instant tree had a circumference of the trunk of five feet at a height measured three feet from the ground and two main branches measuring four feet and three feet in circumference at a height of six feet from the ground. The parentage of this new variety is not known, but the fruit has many characteristics similar but not identical to the 'Bombay' variety of mango and is monoembryonic.

Figure 2:
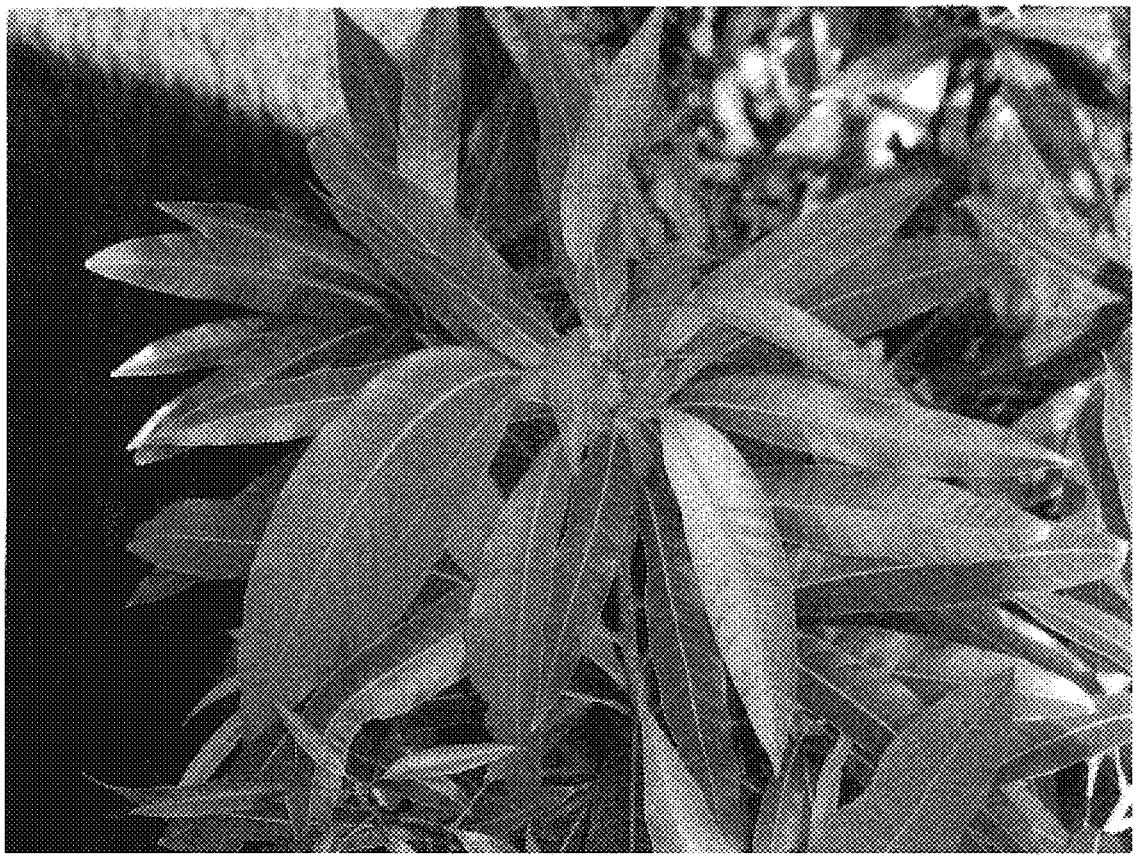
FIG. 2 illustrates the foliage of the mango tree.

This new mango variety has been asexually reproduced. Scions were grafted to 'Turpentine' seedling trees. The characteristics that make the new mango a very desirable variety are the excellence of the fruit quality and its handling and storage ability. As shown in FIG. 2, the foliage of the new mango tree is of average density.

Figure 3:
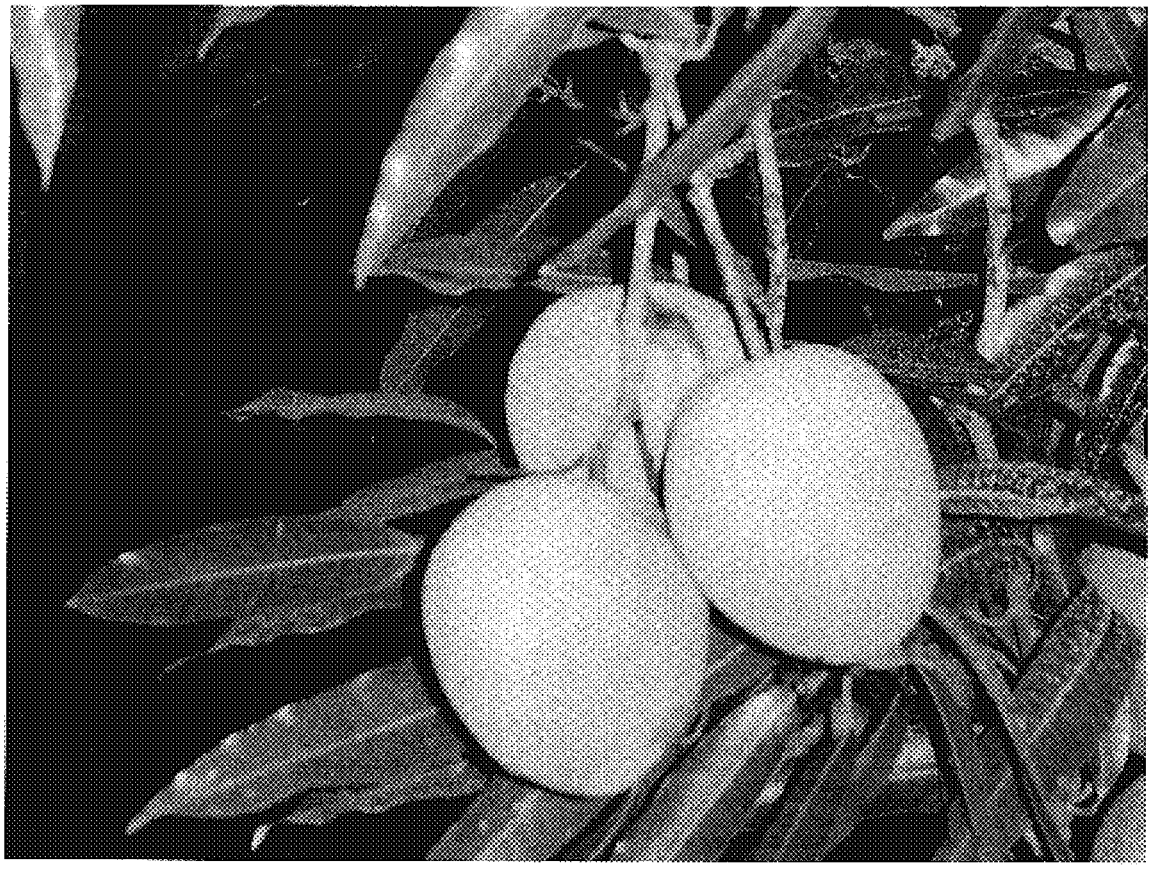
FIG. 3 shows an unripe mango.
Figure 4:
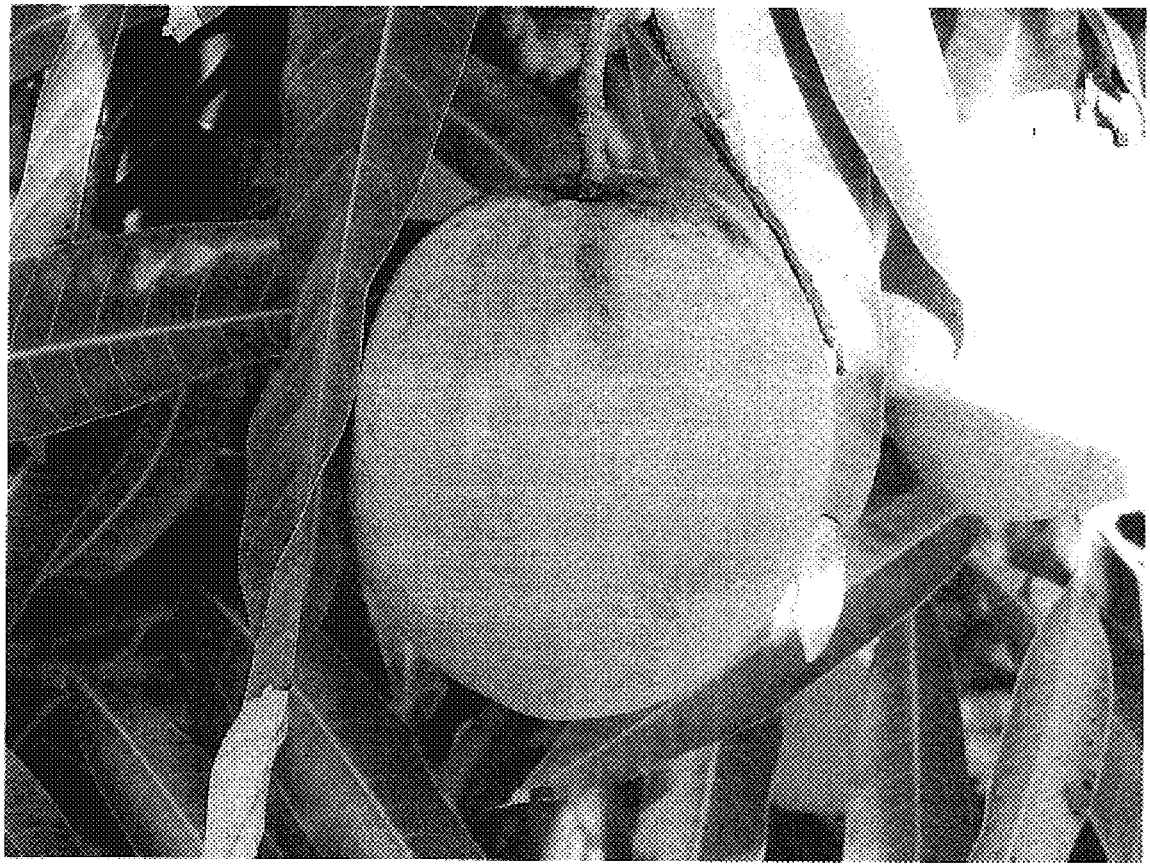
FIG. 4 illustrates a mature mango.

The mango tree blossoms in March, and its fruit matures in July and August. It bears a large plump fruit similar in shape to the mango named 'Bombay Green'. The average weight of the new mango fruit is 13 to 18 ounces when mature. As shown in FIG. 3, the new mango has a color in the Green Group 133D when immature. As the fruits mature, those exposed to direct sunlight take on a blush in the Purple Violet Group 80A, as shown in FIG. 4. A mature mango is approximately 3½ to 4½ inches in length and 2½ to 3½ inches in width.

Figure 5:
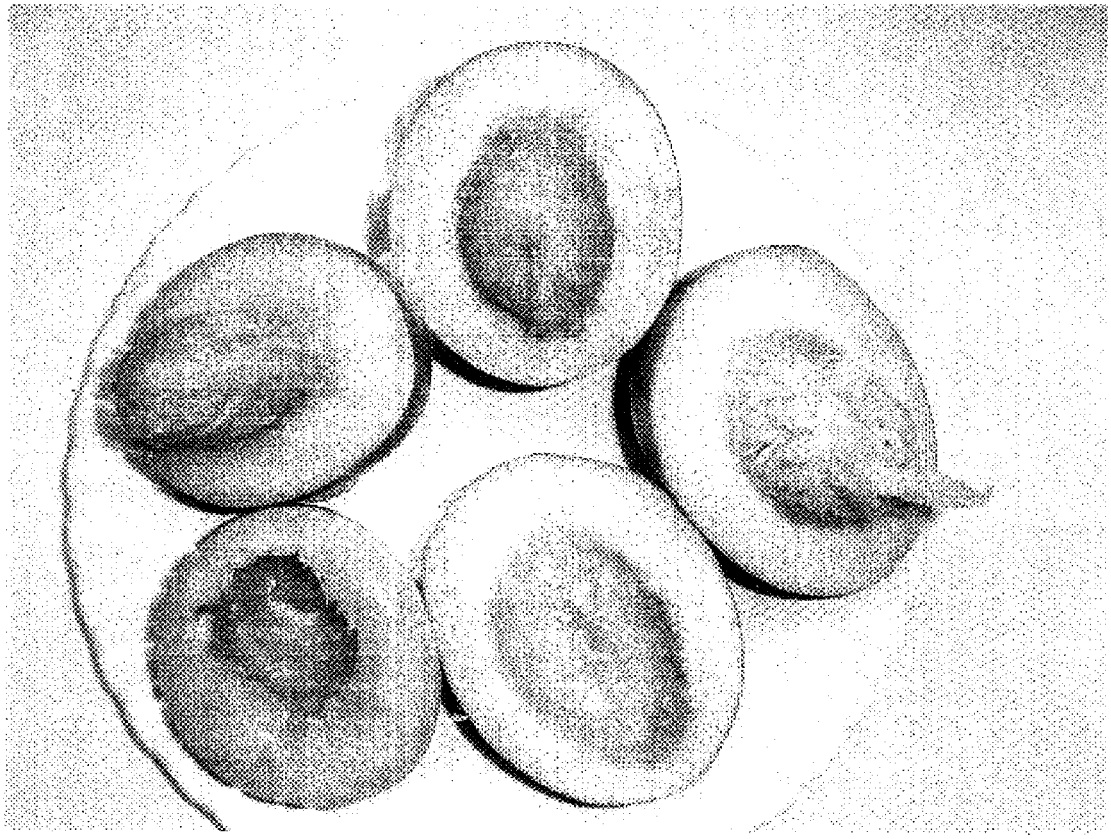
FIG. 5 shows the flesh of the mango.

Referring now to FIG. 5, the flesh of the new mango is bright yellow to gold (Yellow-Orange Group 17C) with only a small amount of fiber attached to the husk of the seed. The seed is small in size, its shape is flat and is only a small percentage of total fruit weight, and the seed is freestone so that the fruit can be served cut in half and eaten with a spoon.

Additional botanical details of the new and distinct variety of tropical mango are as follows, wherein descriptions follow IPGRI Descriptors for Mangos, and color descriptors follow those published by The Royal Horticultural Society:

Tree:
- *Tree vigor.*—Medium.
- *Tree size.*—Medium (30 feet).
- *Tree diameter.*—30 feet east to west.
- *Tree growth habitat.*—Spreading.
- *Tree age.*—>45 years.
- *Tree productivity.*—Very good.
- *Tree regularity.*—Alternate, but not to the extreme.

Trunk:
- *Size.*—Circumference 68 inches.
- *Size branch east.*—Circumference 52 inches.
- *Size branch west.*—Circumference 39 inches.
- *Surface texture.*—Very rough deeply cracked.
- *Color.*—Grayed Yellow 161D.

Branches:
- *Surface texture.*—Less rough than trunk.
- *Size.*—Variable depending on age of growth.
- *Color.*—Same as trunk.
- *Color branch 1 year old.*—Green group 141B.

Leaves:

Size:
- *Average length.*—10–15 inches.
- *Average width.*—2–2¾ inches.
- *Shape.*—Oval-lanceolate. Apex.—Sub-Acuminate. Base.—Acute.
- *Leaf margin.*—Wavy but midrib is straight.
- *Leaf pubescence.*—Absent.
- *Color of young leaf.*—Grayed Red Group 178 B both upper and lower surface.
- *Color of mature leaf.*—Green Group 135 A (upper surface).
- *Color of mature leaf.*—Green Group 137 C (lower surface).
- *Leaf thickness.*—1/32 of an inch.
- *Odor of crushed leaves.*—Distinct Caribbean mango variety, 'Bombay'.
- *Leaf orientation.*—Horizontal.
- *Leaf venation.*—Medium.

Petioles:
- *Petiole length.*—1½–2½ inches.
- *Petiole width.*—⅛ inch average.
- *Petiole color.*—Green Group 143 A.
- *Thickness of pelvinus.*—Thick and tapering.

Fruit:
- *Fruit weight.*—13–18 ounces.
- *Fruit size.*—(side view). Width.—3⁵⁄₁₆ to 4⅜ inches. Height.—4¹⁄₁₆–4⅜ inches. Fruit shape.—Roundish oblique.
- *Shape of apex.*—Obtuse.
- *Forms of the shoulder.*—Rounded.
- *Forms of the cavity.*—Deep.
- *Insertion of stalk.*—Square.

*Form of the beak.*—Small point.
*Skin of the fruit.*—Thin and tough.
*Mango fruit production.*—Average 25 tons per acre.

Flesh of the fruit:
*Texture.*—Firm, melting and juicy.
*Color.*—Deep Orange, Orange Group 26A.
*Flavor.*—Rich aromatic, sweet with a slight spiciness.
*Fiber.*—None.
*Aroma.*—Pleasant.
*Fruit count per panicle.*—Many.
*Susceptibility to bruising.*—Not easily.
*Susceptibility to wind.*—Low.
*Storage.*—The fruit can be harvested mature green or mature and stores well, ripening to produce excellent quality ripe fruit. The period of storage can be as long as 30 days, under controlled storage conditions.
*Disease susceptibility.*—Low.

*Color of fruit.*—
*Color of immature fruit.*—Green Group 133D.
*Color of immature fruit with direct sunlight.*—A blush in the Purple Violet Group 80A.
*Color of ripe fruit that had no blush.*—Orange group 25A.
*Color of ripe fruit that had purple blush.*—Red Purple Group 60 A blush and Orange Group 25A background.

Fruit stalk attachment:
*Immature fruit.*—Strong.
*Fully mature fruit.*—Weak.

Stone:
*Stone length.*—Average 3 1/16 inches.
*Stone width.*—Average 1½ inches.
*Stone depth.*—Average ½ inch.
*Stone weight.*—One ounce average.
*Stone venation.*—Parallel.
*Stone fiber.*—Low.
*Adherence of fiber to stone.*—Strong.
*Texture of stone fiber.*—Stone.
*Stone.*—Freestone.

Inflorescence:
*Number of years to first flowering.*—3 years.
*Secondary flowering.*—Intermediate.
*Regularity of flowering.*—Alternate, but not to the extreme.
*Inflorescence position.*—Terminal.
*Inflorescence axis growth habit.*—Semi-erect.
*Inflorescence shape.*—Broadly pyramidal.
*Inflorescence length.*—7–12 inches.
*Inflorescence width.*—7–10 inches.
*Peduncle length.*—1–4 inches.
*Pubescence of inflorescence.*—None.
*Presence of leafy tracts.*—Present depending on the year.
*Density of flowers in inflorescence.*—Dense.
*Type of flower.*—Pentamerous.
*Inflorescence color.*—Whitish.

What is claimed is:

1. A new and distinct variety of tropical mango tree substantially as described and illustrated, having a mature fruit with good keeping qualities and which is freestone.

* * * * *